United States Patent [19]

Vesselinova-Jenkins

[11] 4,338,299

[45] Jul. 6, 1982

[54] VACCINE AGAINST PERTUSSIS

[75] Inventor: Chrisso K. Vesselinova-Jenkins, Blackwood, Wales

[73] Assignee: DSO "Pharmachim", Sofia, Bulgaria

[21] Appl. No.: 207,434

[22] Filed: Nov. 17, 1980

[51] Int. Cl.$^3$ ............................................... A61K 39/10
[52] U.S. Cl. .......................................... 424/92; 424/93
[58] Field of Search .............................. 424/92, 93, 88; 435/253

[56] References Cited

U.S. PATENT DOCUMENTS 3,465,078 9/1969 Spiesel et al. ........................... 424/92
4,029,766 6/1977 Helting ................................... 424/92

OTHER PUBLICATIONS

Chemical Abstracts, vol. 93, p. 68, Abstract No. 143031s, 1980.
Chemical Abstracts, vol. 79, p. 40, Abstract No. 73753p, 1973.
Chemical Abstracts, vol. 91, p. 469, Abstract No. 191184z, 1979.

*Primary Examiner*—Blondel Hazel
*Attorney, Agent, or Firm*—Karl F. Ross

[57] ABSTRACT

A vaccine effective against pertussis in infants, administered orally, comprises live bacteria of the Bordetella pertussis strain EM 1964.

5 Claims, No Drawings

VACCINE AGAINST PERTUSSIS

The invention relates to a vaccine against pertussis, given per os, in order to prevent babies from contracting pertussis.

The vaccine currently employed to prevent pertussis consists of killed *Bordetella pertussis* bacteriae.

The disadvantages of said vaccine are that it causes several allergic reactions, as well as complications on the part of the central nervous system, such as convulsions and encephalopathies.

References:

1. Kulenkampff, M., Schwartzman, J. S., and Wilson, J. (1974). Neurological complications of pertussis inoculation.—Archives of Disease in Childh 49, 46–49.
2. Madsen, T. (1933). Vaccination against whooping cough.—Journal of the American M Association, 101, 187–188.

The object of the invention is to provide a vaccine against pertussis which is free of side effects, such as allergic reactions associated with complications of the central nervous system.

This object is accomplished through a pertussis vaccine which consists of live bacteriae of *Bordetella pertussis* strain number EM 1964.

The advantages of the vaccine according to the invention are as follow:

High immunogenicity after Kendrick and minimal toxicity.

Allergic reactions and complications of the central nervous system have not been observed as a result of its application.

The nature of the vaccine according to the invention is explained with the following example:

The vaccine consists of live bacteriae of *Bordetella pertussis strain EM* 1964. It is given in doses varying from 3 million to 3 billion microbe organism in 1 ml. physiological salt solution and is given in two portions in 10 days interval using equal doses of 1.5 million to 1.5 billion microbeorganisms per administration. The strain EM 1964 was isolated from urine of a child ill with pertussis and was registered in the—State Institute for Drug Control, Sofia bl. V. Zaimov, 26 under N. 321, from 26.12.1968.

The strain was finally typified in

Public Health Laboratories, Cardiff,

Department of Microbiology University of Manchister, Great Britain.

Pertussis vaccine is obtained by cultivating of the strain of Borget-Genou media for 48 hours at 37° C. The suspension is made in physiological salt solution and diluted in doses shown in Tables 1 and 2 which follow. The standardization is done according to international standards.

The vaccine is given per os.

From Table 1 it is evident that mortality is avoided in mice, immunized with live vaccine per so after being infected with virulent pertussis bacteriae, while 100% of the non-immunized die.

TABLE 1

Mouse protection test of a live experimental vaccine strain *Bordetella pertussis* EM 1964 after Kendrick

| Route of active immunization | Group No. | Dose of vaccine No. of organism | no. of mice tested | Intracerebral innoculation with 100LD$_{50}$ of *Bordetella pertussis* 18323 No. died | % of survival |
|---|---|---|---|---|---|
| Intraperitoneal | 1 | 3 billion | 10 | 2 | 80% |
|  | 2 | 300 million | 17 | 1 | 94.12 |
|  | 3 | 30 million | 11 | — | 100 |
|  | 4 | 3 million | 16 | 7 | 56.35 |
|  | 5 | control | 10 | 10 | 0 |
| Per os | 1 | 3 billion | 18 | 2 | 89.89 |
|  | 2 | 300 million | 14 | 2 | 85.71 |
|  | 3 | 30 million | 17 | 2 | 88.24 |
|  | 4 | 3 million | 12 | — | 100 |
|  | 5 | control | 8 | 8 | 0 |

According to Table 1 from 85.71% to 100% of the white mice immunized per os with doses from 3 million to 3 billion (for the different groups of mice), survive after intracerebral innoculation with LD$_{50}$ of the highly virulent strain of *Bordetella pertussis* 18323. At the same time 100% of the non-immunized control mice die.

Experimental animals (second series) were immunized with identical doses by introducing the vaccine directly in the organism but parenterally by intraperitoneal injection.

It gives approximately the same results and protects the mice 56.35%–100%.

TABLE 2

Toxicity of the live *petussis* vaccine in white mice

| Methods of immunization | Group No. of mice | Single dose of vaccine No. of organisms | Immunization toxicity after 1st dose | 2nd dose | Total % of mortality (1st + 2nd doses) |
|---|---|---|---|---|---|
| Intraperitoneal | 1 | 1.5 billion | 2/16 | 4/14 | 37.5 |
|  | 2 | 150 million | 0/19 | 2/19 | 10.5 |
|  | 3 | 15 million | 0/11 | 0/11 | 0 |
|  | 4 | 1.5 million | 2/18 | 0/16 | 11.1 |
|  | 5 | control | 1/10 | 0/9 | 10 |
| Per os | 1 | 1.5 billion | 0/18 | 0/18 | 0 |
|  | 2 | 150 million | 0/14 | 0/14 | 0 |
|  | 3 | 15 million | 1/20 | 2/19 | 15 |
|  | 4 | 1.5 million | 0/13 | 1/13 | 7 |
|  | 5 | control | 1/10 | 0/9 | 10 |

The denominator signifies the number of the immunized mice and the numerator the number of the dead ones.

The toxic effect of the vaccine, depending on the doses and the method of application, shows that there is a comparatively higher percentage of mortality with those mice which were immunized intraperitoneally or innoculated with a larger dose (3 billion pertussis bacteriae). With the mice immunized intraperitoneally, mortality after the second dose of immunization increases twice in comparison with the first dose. It is probably a result of some allergic reactions caused by the introduction of the second dose of vaccine. In the remaining subgroups of experimental animals the mortality after the first and second dose of immunization given per os is minimal. This proves that the vaccine introduced in the organism by the alimentary tract does not cause allergic reactions.

According to Table 2 minimum deaths occur after immunization with live vaccine given per os. Therefor the minimum toxicity is determined by the natural enteral way of introduction of the vaccine as well as the dose.

I claim:

1. A pertussis vaccine which comprises live pertussis bacteria of the *Bordetella pertussis* strain EM 1964 in a pertussis immunization dosage.

2. A vaccine as claimed in claim 1, which is in a form suitable for oral administration.

3. A vaccine as claimed in claim 1 or 2 which is in unit dosage form, each dosage containing from 3 million to 3 billion microbe organisms per ml.

4. A method of preventing pertussis in a susceptible subject which comprises the step of administering to said subject an effective amount of the vaccine defined in claim 1.

5. The method of preventing pertussis as defined in claim 4 wherein the vaccine is orally administered.